(12) United States Patent
Hodgkinson et al.

(10) Patent No.: US 9,295,466 B2
(45) Date of Patent: Mar. 29, 2016

(54) SURGICAL APPARATUS INCLUDING SURGICAL BUTTRESS

(71) Applicant: Covidien LP, Mansfield, MA (US)

(72) Inventors: Gerald N. Hodgkinson, Guilford, CT (US); Scott J. Prior, Shelton, CT (US)

(73) Assignee: Covidien LP, Mansfield, MA (US)

( * ) Notice: Subject to any disclaimer, the term of this patent is extended or adjusted under 35 U.S.C. 154(b) by 662 days.

(21) Appl. No.: 13/690,362

(22) Filed: Nov. 30, 2012

(65) Prior Publication Data

US 2014/0151431 A1    Jun. 5, 2014

(51) Int. Cl.
*A61B 17/068*  (2006.01)
*A61B 17/072*  (2006.01)

(52) U.S. Cl.
CPC ......... *A61B 17/068* (2013.01); *A61B 17/07292* (2013.01); *A61B 2017/07264* (2013.01); *A61B 2017/07271* (2013.01)

(58) Field of Classification Search
CPC .............................. A61B 17/00; A61B 17/068
USPC ............................................ 227/175.1–182.1
See application file for complete search history.

(56) References Cited

U.S. PATENT DOCUMENTS

| | | | |
|---|---|---|---|
| 3,054,406 | A | 9/1962 | Usher |
| 3,079,606 | A | 3/1963 | Bobrov et al. |
| 3,124,136 | A | 3/1964 | Usher |
| 3,490,675 | A | 1/1970 | Green et al. |
| 3,499,591 | A | 3/1970 | Green |
| 4,347,847 | A | 9/1982 | Usher |
| 4,354,628 | A | 10/1982 | Green |
| 4,429,695 | A | 2/1984 | Green |
| 4,452,245 | A | 6/1984 | Usher |
| 4,605,730 | A | 8/1986 | Shalaby et al. |
| 4,655,221 | A | 4/1987 | Devereux |
| 4,834,090 | A | 5/1989 | Moore |

(Continued)

FOREIGN PATENT DOCUMENTS

| | | |
|---|---|---|
| CA | 2 667 434 | 5/2008 |
| CN | 101310680 A | 11/2008 |

(Continued)

OTHER PUBLICATIONS

International Search Report corresponding to European Application No. EP 05 02 2585.3, completed on Jan. 25, 2006 and mailed on Feb. 3, 2006; 4 pages.

(Continued)

*Primary Examiner* — Hemant M Desai
*Assistant Examiner* — Valentin Neacsu (57) ABSTRACT

A surgical stapling apparatus includes a housing and an end effector secured to the housing. The housing supports a knife assembly including a knife. The end effector has first and second jaw members. One or both of the first and second jaw members define a knife channel. The first jaw member defines fastener slots and the second jaw member defines fastener pockets. One or more of the knife channel, the fastener slots, and the fastener pockets includes lateral recesses. Fasteners are disposed in the fastener slots and formed by the fastener pockets. One or more surgical buttresses have a body that overlies one or both of the fastener slots and the fastener pockets. Portions of the body of the one or more surgical buttresses are disposed within the lateral recesses to secure the one or more surgical buttresses to one or both of the first jaw member and the second jaw member.

11 Claims, 5 Drawing Sheets

(56) References Cited

U.S. PATENT DOCUMENTS

| | | | |
|---|---|---|---|
| 4,838,884 | A | 6/1989 | Dumican et al. |
| 4,927,640 | A | 5/1990 | Dahlinder et al. |
| 4,930,674 | A | 6/1990 | Barak |
| 5,002,551 | A | 3/1991 | Linsky et al. |
| 5,014,899 | A | 5/1991 | Presty et al. |
| 5,040,715 | A | 8/1991 | Green et al. |
| 5,065,929 | A | 11/1991 | Schulze et al. |
| 5,137,198 | A | 8/1992 | Nobis et al. |
| 5,205,459 | A | 4/1993 | Brinkerhoff et al. |
| 5,263,629 | A | 11/1993 | Trumbull et al. |
| 5,307,976 | A | 5/1994 | Olson et al. |
| 5,312,023 | A | 5/1994 | Green et al. |
| 5,314,471 | A | 5/1994 | Brauker et al. |
| 5,318,221 | A | 6/1994 | Green et al. |
| 5,326,013 | A | 7/1994 | Green et al. |
| 5,332,142 | A | 7/1994 | Robinson et al. |
| 5,344,454 | A | 9/1994 | Clarke et al. |
| 5,392,979 | A | 2/1995 | Green et al. |
| 5,397,324 | A | 3/1995 | Carroll et al. |
| 5,425,745 | A | 6/1995 | Green et al. |
| 5,441,193 | A | 8/1995 | Gravener |
| 5,441,507 | A | 8/1995 | Wilk et al. |
| 5,443,198 | A | 8/1995 | Viola et al. |
| 5,468,253 | A * | 11/1995 | Bezwada et al. .............. 606/230 |
| 5,503,638 | A | 4/1996 | Cooper et al. |
| 5,542,594 | A | 8/1996 | McKean et al. |
| 5,549,628 | A | 8/1996 | Cooper et al. |
| 5,575,803 | A | 11/1996 | Cooper et al. |
| 5,653,756 | A | 8/1997 | Clarke et al. |
| 5,683,809 | A | 11/1997 | Freeman et al. |
| 5,690,675 | A | 11/1997 | Sawyer et al. |
| 5,702,409 | A | 12/1997 | Rayburn et al. |
| 5,752,965 | A | 5/1998 | Francis et al. |
| 5,762,256 | A | 6/1998 | Mastri et al. |
| 5,766,188 | A | 6/1998 | Igaki |
| 5,769,892 | A | 6/1998 | Kingwell |
| 5,782,396 | A | 7/1998 | Mastri et al. |
| 5,799,857 | A | 9/1998 | Robertson et al. |
| 5,810,855 | A | 9/1998 | Rayburn et al. |
| 5,814,057 | A | 9/1998 | Oi et al. |
| 5,833,695 | A | 11/1998 | Yoon |
| 5,843,096 | A | 12/1998 | Igaki et al. |
| 5,865,361 | A | 2/1999 | Milliman et al. |
| 5,895,412 | A | 4/1999 | Tucker |
| 5,895,415 | A | 4/1999 | Chow et al. |
| 5,902,312 | A | 5/1999 | Frater et al. |
| 5,908,427 | A | 6/1999 | McKean et al. |
| 5,915,616 | A | 6/1999 | Viola et al. |
| 5,931,847 | A | 8/1999 | Bittner et al. |
| 5,964,394 | A | 10/1999 | Robertson |
| 5,964,774 | A | 10/1999 | McKean et al. |
| 5,997,895 | A | 12/1999 | Narotam et al. |
| 6,019,791 | A | 2/2000 | Wood |
| 6,030,392 | A | 2/2000 | Dakov et al. |
| 6,032,849 | A | 3/2000 | Mastri et al. |
| 6,045,560 | A | 4/2000 | McKean et al. |
| 6,063,097 | A | 5/2000 | Oi et al. |
| 6,080,169 | A | 6/2000 | Turtel |
| 6,099,551 | A | 8/2000 | Gabbay |
| 6,149,667 | A | 11/2000 | Hovland et al. |
| 6,155,265 | A | 12/2000 | Hammerslag |
| 6,202,914 | B1 | 3/2001 | Geiste |
| 6,210,439 | B1 | 4/2001 | Firmin et al. |
| 6,214,020 | B1 | 4/2001 | Mulhauser et al. |
| 6,241,139 | B1 | 6/2001 | Milliman et al. |
| 6,258,107 | B1 | 7/2001 | Balazs et al. |
| 6,267,772 | B1 | 7/2001 | Mulhauser et al. |
| 6,273,897 | B1 | 8/2001 | Dalessandro et al. |
| 6,280,453 | B1 | 8/2001 | Kugel et al. |
| 6,299,631 | B1 | 10/2001 | Shalaby |
| 6,312,457 | B1 | 11/2001 | DiMatteo et al. |
| 6,312,474 | B1 | 11/2001 | Francis et al. |
| 6,325,810 | B1 | 12/2001 | Hamilton et al. |
| 6,436,030 | B2 | 8/2002 | Rehil |
| 6,454,780 | B1 | 9/2002 | Wallace |
| 6,461,368 | B2 | 10/2002 | Fogarty et al. |
| 6,503,257 | B2 | 1/2003 | Grant et al. |
| 6,514,283 | B2 | 2/2003 | DiMatteo et al. |
| 6,517,566 | B1 | 2/2003 | Hovland et al. |
| 6,551,356 | B2 | 4/2003 | Rousseau |
| 6,592,597 | B2 | 7/2003 | Grant et al. |
| 6,638,285 | B2 | 10/2003 | Gabbay |
| 6,652,594 | B2 | 11/2003 | Francis et al. |
| 6,656,193 | B2 | 12/2003 | Grant et al. |
| 6,669,735 | B1 | 12/2003 | Pelissier |
| 6,677,258 | B2 | 1/2004 | Carroll et al. |
| 6,685,714 | B2 | 2/2004 | Rousseau |
| 6,702,828 | B2 | 3/2004 | Whayne |
| 6,704,210 | B1 | 3/2004 | Myers |
| 6,723,114 | B2 | 4/2004 | Shalaby |
| 6,726,706 | B2 | 4/2004 | Dominguez |
| 6,736,823 | B2 | 5/2004 | Darois et al. |
| 6,736,854 | B2 | 5/2004 | Vadurro et al. |
| 6,746,458 | B1 | 6/2004 | Cloud |
| 6,773,458 | B1 | 8/2004 | Brauker et al. |
| 6,896,684 | B2 | 5/2005 | Monassevitch et al. |
| 6,927,315 | B1 | 8/2005 | Heinecke et al. |
| 6,939,358 | B2 | 9/2005 | Palacios et al. |
| 6,946,196 | B2 | 9/2005 | Foss |
| 6,959,851 | B2 | 11/2005 | Heinrich |
| 7,087,065 | B2 | 8/2006 | Ulmsten et al. |
| 7,108,701 | B2 | 9/2006 | Evens et al. |
| 7,128,748 | B2 | 10/2006 | Mooradian et al. |
| 7,134,438 | B2 | 11/2006 | Makower et al. |
| 7,141,055 | B2 | 11/2006 | Abrams et al. |
| 7,147,138 | B2 | 12/2006 | Shelton, IV |
| 7,160,299 | B2 | 1/2007 | Baily |
| 7,232,449 | B2 | 6/2007 | Sharkawy et al. |
| 7,241,300 | B2 | 7/2007 | Sharkawy et al. |
| 7,307,031 | B2 | 12/2007 | Carroll et al. |
| 7,311,720 | B2 | 12/2007 | Mueller et al. |
| 7,377,928 | B2 | 5/2008 | Zubik et al. |
| 7,434,717 | B2 | 10/2008 | Shelton, IV et al. |
| 7,438,209 | B1 | 10/2008 | Hess et al. |
| 7,547,312 | B2 | 6/2009 | Bauman et al. |
| 7,559,937 | B2 | 7/2009 | de la Torre et al. |
| 7,571,845 | B2 | 8/2009 | Viola |
| 7,594,921 | B2 | 9/2009 | Browning |
| 7,604,151 | B2 | 10/2009 | Hess et al. |
| 7,665,646 | B2 | 2/2010 | Prommersberger |
| 7,666,198 | B2 | 2/2010 | Suyker et al. |
| 7,669,747 | B2 | 3/2010 | Weisenburgh, II et al. |
| 7,717,313 | B2 | 5/2010 | Bettuchi et al. |
| 7,722,642 | B2 | 5/2010 | Williamson, IV |
| 7,744,627 | B2 | 6/2010 | Orban, III et al. |
| 7,776,060 | B2 | 8/2010 | Mooradian et al. |
| 7,793,813 | B2 | 9/2010 | Bettuchi |
| 7,794,475 | B2 | 9/2010 | Hess et al. |
| 7,799,026 | B2 | 9/2010 | Schechter et al. |
| 7,823,592 | B2 | 11/2010 | Bettuchi et al. |
| 7,824,420 | B2 | 11/2010 | Eldridge et al. |
| 7,845,533 | B2 | 12/2010 | Marczyk et al. |
| 7,845,536 | B2 | 12/2010 | Viola et al. |
| 7,846,149 | B2 | 12/2010 | Jankowski |
| 7,892,247 | B2 | 2/2011 | Conston et al. |
| 7,909,224 | B2 | 3/2011 | Prommersberger |
| 7,909,837 | B2 | 3/2011 | Crows et al. |
| 7,938,307 | B2 | 5/2011 | Bettuchi |
| 7,942,890 | B2 | 5/2011 | D'Agostino et al. |
| 7,950,561 | B2 | 5/2011 | Aranyi |
| 7,951,166 | B2 | 5/2011 | Orban |
| 7,967,179 | B2 | 6/2011 | Olson |
| 7,988,027 | B2 | 8/2011 | Olson |
| 8,011,550 | B2 | 9/2011 | Aranyi |
| 8,011,555 | B2 | 9/2011 | Tarinelli et al. |
| 8,016,177 | B2 | 9/2011 | Bettuchi |
| 8,016,178 | B2 | 9/2011 | Olson |
| 8,028,883 | B2 | 10/2011 | Stopek |
| 8,062,330 | B2 | 11/2011 | Prommersberger |
| 8,083,119 | B2 | 12/2011 | Prommersberger |
| 8,123,766 | B2 | 2/2012 | Bauman |
| 8,123,767 | B2 | 2/2012 | Bauman |
| 8,146,791 | B2 | 4/2012 | Bettuchi |
| 8,157,149 | B2 | 4/2012 | Olson |

(56) References Cited

U.S. PATENT DOCUMENTS

| | | | |
|---|---|---|---|
| 8,157,151 B2 | 4/2012 | Ingmanson |
| 8,167,895 B2 | 5/2012 | D'Agostino |
| 8,178,746 B2 | 5/2012 | Hildeberg et al. |
| 8,192,460 B2 | 6/2012 | Orban |
| 8,210,414 B2 | 7/2012 | Bettuchi |
| 8,225,799 B2 | 7/2012 | Bettuchi |
| 8,225,981 B2 | 7/2012 | Criscuolo et al. |
| 8,231,043 B2 | 7/2012 | Tarinelli |
| 8,235,273 B2 | 8/2012 | Olson |
| 8,245,901 B2 | 8/2012 | Stopek |
| 8,256,654 B2 | 9/2012 | Bettuchi |
| 8,257,391 B2 | 9/2012 | Orban |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi |
| 8,308,046 B2 | 11/2012 | Prommersberger |
| 8,312,885 B2 | 11/2012 | Bettuchi |
| 8,313,014 B2 | 11/2012 | Bettuchi |
| 8,348,126 B2 | 1/2013 | Olson |
| 8,348,130 B2 | 1/2013 | Shah |
| 8,365,972 B2 | 2/2013 | Aranyi et al. |
| 8,371,491 B2 | 2/2013 | Huitema |
| 8,371,492 B2 | 2/2013 | Aranyi |
| 8,371,493 B2 | 2/2013 | Aranyi |
| 8,393,514 B2 | 3/2013 | Shelton, IV |
| 8,408,440 B2 | 4/2013 | Olson |
| 8,413,869 B2 | 4/2013 | Heinrich |
| 8,413,871 B2 | 4/2013 | Racenet |
| 8,424,742 B2 | 4/2013 | Bettuchi |
| 8,453,652 B2 | 6/2013 | Stopek |
| 8,453,904 B2 | 6/2013 | Eskaros |
| 8,453,909 B2 | 6/2013 | Olson |
| 8,453,910 B2 | 6/2013 | Bettuchi |
| 8,464,925 B2 | 6/2013 | Hull et al. |
| 8,474,677 B2 | 7/2013 | Woodard, Jr. |
| 8,479,968 B2 | 7/2013 | Hodgkinson |
| 8,485,414 B2 | 7/2013 | Criscuolo et al. |
| 8,496,683 B2 | 7/2013 | Prommersberger |
| 8,511,533 B2 | 8/2013 | Viola |
| 8,512,402 B2 | 8/2013 | Marczyk |
| 8,529,600 B2 | 9/2013 | Woodard, Jr. |
| 8,540,131 B2 | 9/2013 | Swayze |
| 8,551,138 B2 | 10/2013 | Orban |
| 8,556,918 B2 | 10/2013 | Bauman |
| 8,561,873 B2 | 10/2013 | Ingmanson |
| 8,584,920 B2 | 11/2013 | Hodgkinson |
| 8,590,762 B2 | 11/2013 | Hess |
| 8,616,430 B2 | 12/2013 | Prommersberger |
| 8,631,989 B2 | 1/2014 | Aranyi |
| 8,646,674 B2 | 2/2014 | Schulte et al. |
| 8,668,129 B2 | 3/2014 | Olson |
| 8,684,250 B2 | 4/2014 | Bettuchi |
| 8,721,703 B2 | 5/2014 | Fowler |
| 8,757,466 B2 | 6/2014 | Olson |
| 8,789,737 B2 | 7/2014 | Hodgkinson |
| 8,820,606 B2 | 9/2014 | Hodgkinson |
| 8,870,050 B2 | 10/2014 | Hodgkinson |
| 8,920,444 B2 | 12/2014 | Hiles et al. |
| 8,939,344 B2 | 1/2015 | Olson et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek et al. |
| 9,016,544 B2 | 4/2015 | Hodgkinson et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 2002/0028243 A1 | 3/2002 | Masters |
| 2002/0091397 A1 | 7/2002 | Chen |
| 2003/0065345 A1 | 4/2003 | Weadock |
| 2003/0083676 A1 | 5/2003 | Wallace |
| 2003/0120284 A1 | 6/2003 | Palacios |
| 2003/0181927 A1 | 9/2003 | Wallace |
| 2003/0183671 A1 | 10/2003 | Mooradian et al. |
| 2003/0208231 A1 | 11/2003 | Williamson, IV et al. |
| 2004/0107006 A1 | 6/2004 | Francis et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0143756 A1 | 6/2005 | Jankowski |
| 2005/0149073 A1 | 7/2005 | Arani et al. |
| 2006/0004407 A1 | 1/2006 | Hiles et al. |
| 2006/0135992 A1 | 6/2006 | Bettuchi |
| 2006/0173470 A1 | 8/2006 | Oray et al. |
| 2006/0178683 A1 | 8/2006 | Shimoji et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0200949 A1 | 8/2008 | Hiles |
| 2008/0220047 A1 | 9/2008 | Sawhney et al. |
| 2008/0230583 A1 | 9/2008 | Heinrich |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |

(56) References Cited

U.S. PATENT DOCUMENTS

| | | |
|---|---|---|
| 2009/0206142 A1 | 8/2009 | Huitema et al. |
| 2009/0206143 A1* | 8/2009 | Huitema et al. ........... 227/176.1 |
| 2009/0218384 A1* | 9/2009 | Aranyi ....................... 227/176.1 |
| 2009/0277944 A9 | 11/2009 | Dalessandro et al. |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0065606 A1 | 3/2010 | Stopek |
| 2010/0065607 A1 | 3/2010 | Orban, III et al. |
| 2010/0072254 A1 | 3/2010 | Aranyi et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2010/0331880 A1 | 12/2010 | Stopek |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0087279 A1 | 4/2011 | Shah et al. |
| 2011/0095070 A1* | 4/2011 | Patel et al. .................. 227/181.1 |
| 2011/0215132 A1 | 9/2011 | Aranyi |
| 2011/0215133 A1* | 9/2011 | Aranyi ....................... 227/180.1 |
| 2012/0074199 A1 | 3/2012 | Olson |
| 2012/0080336 A1 | 4/2012 | Shelton |
| 2012/0083723 A1 | 4/2012 | Vitaris et al. |
| 2012/0145767 A1* | 6/2012 | Shah et al. .................. 227/180.1 |
| 2012/0168486 A1 | 7/2012 | Ingmanson et al. |
| 2012/0187179 A1 | 7/2012 | Gleiman |
| 2012/0197272 A1 | 8/2012 | Oray et al. |
| 2012/0241491 A1* | 9/2012 | Aldridge et al. ........... 227/175.1 |
| 2012/0241492 A1* | 9/2012 | Shelton et al. ............. 227/175.1 |
| 2012/0241499 A1 | 9/2012 | Baxter et al. |
| 2012/0273547 A1 | 11/2012 | Hodgkinson et al. |
| 2013/0037596 A1 | 2/2013 | Bear et al. |
| 2013/0105548 A1 | 5/2013 | Hodgkinson |
| 2013/0105553 A1 | 5/2013 | Racenet |
| 2013/0112732 A1 | 5/2013 | Aranyi |
| 2013/0112733 A1 | 5/2013 | Aranyi |
| 2013/0146641 A1 | 6/2013 | Shelton |
| 2013/0153633 A1 | 6/2013 | Casasanta |
| 2013/0153634 A1 | 6/2013 | Carter |
| 2013/0153635 A1 | 6/2013 | Hodgkinson |
| 2013/0153636 A1 | 6/2013 | Shelton |
| 2013/0153638 A1 | 6/2013 | Carter |
| 2013/0153639 A1 | 6/2013 | Hodgkinson |
| 2013/0153640 A1 | 6/2013 | Hodgkinson |
| 2013/0153641 A1 | 6/2013 | Shelton |
| 2013/0161374 A1 | 6/2013 | Swayze |
| 2013/0181031 A1 | 7/2013 | Olson |
| 2013/0193186 A1 | 8/2013 | Racenet |
| 2013/0193190 A1 | 8/2013 | Carter |
| 2013/0193191 A1 | 8/2013 | Stevenson |
| 2013/0193192 A1 | 8/2013 | Casasanta |
| 2013/0209659 A1 | 8/2013 | Racenet |
| 2013/0221062 A1 | 8/2013 | Hodgkinson |
| 2013/0240600 A1 | 9/2013 | Bettuchi |
| 2013/0240601 A1 | 9/2013 | Bettuchi |
| 2013/0240602 A1 | 9/2013 | Stopek |
| 2013/0256380 A1 | 10/2013 | Schmid et al. |
| 2013/0277411 A1 | 10/2013 | Hodgkinson |
| 2013/0306707 A1 | 11/2013 | Viola |
| 2013/0310873 A1 | 11/2013 | Prommersberger |
| 2013/0327807 A1 | 12/2013 | Olson |
| 2014/0012317 A1 | 1/2014 | Orban |
| 2014/0021242 A1 | 1/2014 | Hodgkinson |
| 2014/0027490 A1 | 1/2014 | Marczyk |
| 2014/0034704 A1 | 2/2014 | Ingmanson |
| 2014/0048580 A1 | 2/2014 | Merchant |
| 2014/0061280 A1 | 3/2014 | Ingmanson |
| 2014/0061281 A1 | 3/2014 | Hodgkinson |
| 2014/0084042 A1 | 3/2014 | Stopek |
| 2014/0097224 A1 | 4/2014 | Prior |
| 2014/0117066 A1 | 5/2014 | Aranyi |
| 2014/0130330 A1 | 5/2014 | Olson |
| 2014/0131418 A1 | 5/2014 | Kostrzewski |
| 2014/0131419 A1 | 5/2014 | Bettuchi |
| 2014/0138423 A1 | 5/2014 | Whitfield |
| 2014/0151431 A1 | 6/2014 | Hodgkinson |
| 2014/0155916 A1 | 6/2014 | Hodgkinson |
| 2014/0158742 A1 | 6/2014 | Stopek |
| 2014/0166721 A1 | 6/2014 | Stevenson |
| 2014/0197224 A1 | 7/2014 | Penna |
| 2014/0203061 A1 | 7/2014 | Hodgkinson |
| 2014/0217147 A1 | 8/2014 | Milliman |
| 2014/0217148 A1 | 8/2014 | Penna |
| 2014/0239046 A1 | 8/2014 | Milliman |
| 2014/0239047 A1 | 8/2014 | Hodgkinson |
| 2014/0252062 A1 | 9/2014 | Mozdzierz |
| 2015/0001276 A1 | 1/2015 | Hodgkinson et al. |
| 2015/0041347 A1 | 2/2015 | Hodgkinson |
| 2015/0097018 A1 | 4/2015 | Hodgkinson |
| 2015/0115015 A1 | 4/2015 | Prescott et al. |
| 2015/0122872 A1 | 5/2015 | Olson et al. |
| 2015/0164503 A1 | 6/2015 | Stevenson et al. |
| 2015/0164506 A1 | 6/2015 | Carter et al. |
| 2015/0164507 A1 | 6/2015 | Carter et al. |
| 2015/0196297 A1 | 7/2015 | (Prommersberger) Stopek et al. |
| 2015/0209033 A1 | 7/2015 | Hodgkinson |
| 2015/0209045 A1 | 7/2015 | Hodgkinson et al. |
| 2015/0209048 A1 | 7/2015 | Carter et al. |

FOREIGN PATENT DOCUMENTS

| | | |
|---|---|---|
| CN | 101332110 A | 12/2008 |
| DE | 1 99 24 311 A1 | 11/2000 |
| EP | 0 594 148 A1 | 4/1994 |
| EP | 0 327 022 B1 | 4/1995 |
| EP | 0 667 119 A1 | 8/1995 |
| EP | 1 064 883 A1 | 1/2001 |
| EP | 1 256 317 A2 | 11/2002 |
| EP | 1 256 318 | 11/2002 |
| EP | 1 520 525 A1 | 4/2005 |
| EP | 1 621 141 A2 | 2/2006 |
| EP | 1 702 570 A2 | 9/2006 |
| EP | 1 759 640 A2 | 3/2007 |
| EP | 1 815 804 A2 | 8/2007 |
| EP | 1 825 820 | 8/2007 |
| EP | 1 929 958 | 6/2008 |
| EP | 1 994 890 A1 | 11/2008 |
| EP | 2 005 894 A2 | 12/2008 |
| EP | 2 005 895 A2 | 12/2008 |
| EP | 2 008 595 A2 | 12/2008 |
| EP | 2 039 308 A2 | 3/2009 |
| EP | 2 090 231 | 8/2009 |
| EP | 2 090 244 | 8/2009 |
| EP | 2 090 252 | 8/2009 |
| EP | 2 163 211 A2 | 3/2010 |
| EP | 2 189 121 A1 | 5/2010 |
| EP | 2 198 787 A1 | 6/2010 |
| EP | 2 236 098 A2 | 10/2010 |
| EP | 2 236 099 | 10/2010 |
| EP | 2 258 282 A2 | 12/2010 |
| EP | 2 292 276 A2 | 3/2011 |
| EP | 2 311 386 | 4/2011 |
| EP | 2 436 348 | 4/2012 |
| EP | 2 462 880 | 6/2012 |
| EP | 2 497 431 A1 | 9/2012 |
| EP | 2 517 637 | 10/2012 |
| EP | 2 586 380 | 5/2013 |
| EP | 2 604 195 | 6/2013 |
| EP | 2 604 197 | 6/2013 |
| EP | 2 620 105 A1 | 7/2013 |
| EP | 2 620 106 | 7/2013 |
| EP | 2 630 922 | 8/2013 |
| EP | 2 644 125 | 10/2013 |
| EP | 2 762 091 A2 | 8/2014 |

(56) References Cited

FOREIGN PATENT DOCUMENTS

| | | |
|---|---|---|
| JP | 2000-166933 | 6/2000 |
| JP | 2002-202213 | 7/2002 |
| JP | 2007-124166 | 5/2007 |
| WO | WO 90/05489 A1 | 5/1990 |
| WO | WO 95/16221 | 6/1995 |
| WO | WO 96/22055 A1 | 7/1996 |
| WO | WO 97/01989 A1 | 1/1997 |
| WO | WO 97/13463 A1 | 4/1997 |
| WO | WO 98/17180 A1 | 4/1998 |
| WO | WO 99/45849 A1 | 9/1999 |
| WO | WO 03/082126 A1 | 10/2003 |
| WO | WO 03/088845 | 10/2003 |
| WO | WO 03/094743 | 11/2003 |
| WO | WO 03/105698 A2 | 12/2003 |
| WO | WO 2005/079675 | 9/2005 |
| WO | WO 2006/023578 A2 | 3/2006 |
| WO | WO 2006/044490 A2 | 4/2006 |
| WO | WO 2006/083748 A1 | 8/2006 |
| WO | WO 2007/121579 A1 | 11/2007 |
| WO | WO 2008/057281 A2 | 5/2008 |
| WO | WO 2008/109125 A1 | 9/2008 |
| WO | WO 2010/075298 A2 | 7/2010 |
| WO | WO 2011/143183 A2 | 11/2011 |
| WO | WO 2012/044848 A1 | 4/2012 |

OTHER PUBLICATIONS

International Search Report corresponding to European Application No. EP 06 00 4598, completed on Jun. 22, 2006; 2 pages.
International Search Report corresponding to European Application No. EP 06 01 6962.0, completed on Jan. 3, 2007 and mailed on Jan. 11, 2007; 10 pages.
International Search Report corresponding to International Application No. PCT/US05/36740, completed on Feb. 20, 2007 and mailed on Mar. 23, 2007; 8 pages.
International Search Report corresponding to International Application No. PCT/US2007/022713, completed on Apr. 21, 2008 and mailed on May 15, 2008; 1 page.
International Search Report corresponding to International Application No. PCT/US2008/002981, completed on Jun. 9, 2008 and mailed on Jun. 26, 2008; 2 pages.
International Search Report corresponding to European Application No. EP 08 25 1779, completed on Jul. 14, 2008 and mailed on Jul. 23, 2008; 5 pages.
International Search Report corresponding to European Application No. EP 08 25 1989.3, completed on Mar. 11, 2010 and mailed on Mar. 24, 2010; 6 pages.
International Search Report corresponding to European Application No. EP 10 25 0639.1, completed on Jun. 17, 2010 and mailed on Jun. 28, 2010; 7 pages.
International Search Report corresponding to European Application No. EP 10 25 0715.9, completed on Jun. 30, 2010 and mailed on Jul. 20, 2010; 3 pages.
International Search Report corresponding to European Application No. EP 05 80 4382.9, completed on Oct. 5, 2010 and mailed on Oct. 12, 2010; 3 pages.
International Search Report corresponding to European Application No. EP 10 25 1437.9, completed on Nov. 22, 2010 and mailed on Dec. 16, 2010; 3 pages.
International Search Report corresponding to European Application No. EP 09 25 2897.5, completed on Feb. 7, 2011 and mailed on Feb. 15, 2011; 3 pages.
International Search Report corresponding to European Application No. EP 10 25 0642.5, completed on Mar. 25, 2011 and mailed on Apr. 4, 2011; 4 pages.
International Search Report corresponding to European Application No. EP 11 18 8309.6, completed on Dec. 15, 2011 and mailed on Jan. 12, 2012; 3 pages.
International Search Report corresponding to European Application No. EP 12 15 2229.6, completed on Feb. 23, 2012 and mailed on Mar. 1, 2012; 4 pages.
International Search Report corresponding to European Application No. EP 12 15 0511.9, completed on Apr. 16, 2012 and mailed on Apr. 24, 2012; 7 pages.
International Search Report corresponding to European Application No. EP 12 15 2541.4, completed on Apr. 23, 2012 and mailed on May 3, 2012; 10 pages.
International Search Report corresponding to European Application No. EP 12 16 5609.4, completed on Jul. 5, 2012 and mailed on Jul. 13, 2012; 8 pages.
International Search Report corresponding to European Application No. EP 12 15 8861.0, completed on Jul. 17, 2012 and mailed on Jul. 24, 2012; 9 pages.
International Search Report corresponding to European Application No. EP 12 16 5878.5, completed on Jul. 24, 2012 and mailed on Aug. 6, 2012; 8 pages.
Extended European Search Report corresponding to EP 13 17 7437.4, completed Sep. 11, 2013 and mailed Sep. 19, 2013; (6 pp).
Extended European Search Report corresponding to EP 13 17 7441.6, completed Sep. 11, 2013 and mailed Sep. 19, 2013; (6 pp).
Extended European Search Report corresponding to EP 07 86 1534.1, completed Sep. 20, 2013 and mailed Sep. 30, 2013; (5 pp).
Extended European Search Report corresponding to EP 13 18 3876.5, completed Oct. 14, 2013 and mailed Oct. 24, 2013; (5 pp).
Extended European Search Report corresponding to EP 13 17 1856.1, completed Oct. 29, 2013 and mailed Nov. 7, 2013; (8 pp).
Extended European Search Report corresponding to EP 13 18 0373.6, completed Oct. 31, 2013 and mailed Nov. 13, 2013; (7 pp).
Extended European Search Report corresponding to EP 13 18 0881.8, completed Nov. 5, 2013 and mailed Nov. 14, 2013; (6 pp).
Extended European Search Report corresponding to EP 13 17 6895.4, completed Nov. 29, 2013 and mailed Dec. 12, 2013; (5 pp).
Extended European Search Report corresponding to EP 13 18 2911.1, completed Dec. 2, 2013 and mailed Dec. 16, 2013; (8 pp).
Extended European Search Report corresponding to EP 10 25 1795.0, completed Dec. 11, 2013 and mailed Dec. 20, 2013; (6 pp).
Extended European Search Report corresponding to EP 13 18 7911.6, completed Jan. 22, 2014 and mailed Jan. 31, 2014; (8 pp).
Extended European Search Report corresponding to EP 14 16 9739.1, completed Aug. 19, 2014 and Aug. 29, 2014; (7 pp).
Extended European Search Report corresponding to EP 14 15 7997.9, completed Sep. 9, 2014 and mailed Sep. 17, 2014; (8 pp).
Extended European Search Report corresponding to EP 14 16 8904.2, completed Sep. 10, 2014 and mailed Sep. 18, 2014; (8 pp).
Extended European Search Report corresponding to EP 13 19 4995.0, completed Jun. 5, 2014 and mailed Oct. 13, 2014; (10 pp).
Extended European Search Report corresponding to EP 13 15 4571.7, completed Oct. 10, 2014 and mailed Oct. 20, 2014; (8 pp).
Extended European Search Report corresponding to EP 14 18 1125.7, completed Oct. 16, 2014 and mailed Oct. 24, 2014; (7 pp).
Extended European Search Report corresponding to EP 14 18 1127.3, completed Oct. 16, 2014 and mailed Nov. 10, 2014; (8 pp).
Extended European Search Report corresponding to EP 14 19 0419.3, completed Mar. 24, 2015 and mailed Mar. 30, 2015; (6 pp).
Extended European Search Report corresponding to EP 13 19 5019.8, completed Mar. 14, 2014 and mailed Mar. 24, 2014; (8 pp).
Extended European Search Report corresponding to EP No. 12 19 1035.0, completed Jan. 11, 2013 and mailed Jan. 18, 2013; 7 pages.
Extended European Search Report corresponding to EP No. 12 18 6175.1, completed Jan. 15, 2013 and mailed Jan. 23, 2013; 7 pages.
Extended European Search Report corresponding to EP No. 12 19 1114.3, completed Jan. 23, 2013 and mailed Jan. 31, 2013; 10 pages.
Extended European Search Report corresponding to EP No. 12 19 2224.9, completed Mar. 14, 2013 and mailed Mar. 26, 2013; 8 pages.
Extended European Search Report corresponding to EP No. 12 19 6911.7, completed Apr. 18, 2013 and mailed Apr. 24, 2013; 8 pages.
Extended European Search Report corresponding to EP 13 19 2123.1, completed Jan. 30, 2014 and mailed Feb. 10, 2014; (8 pp).
Extended European Search Report corresponding to EP 13 19 2111.6, completed Feb. 13, 2014 and mailed Feb. 27, 2014; (10 pp).
Extended European Search Report corresponding to EP 13 19 5919.9, completed Feb. 10, 2014 and mailed Mar. 3, 2014; (7 pp).
Extended European Search Report corresponding to EP 08 72 6500.5, completed Feb. 20, 2014 and mailed Mar. 3, 2014; (7 pp).

(56) References Cited

OTHER PUBLICATIONS

Extended European Search Report corresponding to EP 13 19 6816.6, completed Mar. 28, 2014 and mailed Apr. 9, 2014; (9 pp).
Extended European Search Report corresponding to EP 13 19 7958.5, completed Apr. 4, 2014 and mailed Apr. 15, 2014; (8 pp).
Extended European Search Report corresponding to EP 13 19 4995.0, completed Jun. 5, 2014 and mailed Jun. 16, 2014; (5 pp).
Extended European Search Report corresponding to EP 14 15 7195.0, completed Jun. 5, 2014 and mailed Jun. 18, 2014; (9 pp).
Extended European Search Report corresponding to EP 14 15 6342.9, completed Jul. 22, 2014 and mailed Jul. 29, 2014; (8 pp).
Extended European Search Report corresponding to EP 12 19 1035.0, completed Jan. 11, 2013 and mailed Jan. 18, 2013; 7 pages.
Extended European Search Report corresponding to EP 12 19 6904.2, completed Mar. 28, 2013 and mailed Jul. 26, 2013; 8 pages.
Extended European Search Report corresponding to EP 12 19 8749.9, completed May 21, 2013 and mailed May 31, 2013; 8 pages.
Extended European Search Report corresponding to EP 07 00 5842.5, completed May 13, 2013 and mailed May 29, 2013; 7 pages.
Extended European Search Report corresponding to EP 12 19 8776.2, completed May 16, 2013 and mailed May 27, 2013; 8 pages.
Extended European Search Report corresponding to EP 13 15 6297.7, completed Jun. 4, 2013 and mailed Jun. 13, 2013; 7 pages.
Extended European Search Report corresponding to EP 13 17 3985,6; completed Aug. 19, 2013 and mailed Aug. 28, 2013; 6 pages.
Extended European Search Report corresponding to EP 13 17 3986.4, completed Aug. 20, 2013 and mailed Aug. 29, 2013; 7 pages.
European Office Action corresponding to counterpart Int'l Appln No. EP 12 198 776.2 dated Apr. 7, 2015.
European Office Action corresponding to counterpart Int'l Appln No. EP 13 156 297.7 dated Apr. 10, 2015.
Australian Examination Report No. 1 corresponding to counterpart Int'l Appln No. AU 2011250822 dated May 18, 2015.
European Office Action corresponding to counterpart Int'l Appln No. EP 12 186 175.1 dated Jun. 1, 2015.
Chinese Office Action corresponding to counterpart Int'l Appln No. CN 201010517292.8 dated Jun. 2, 2015.
Extended European Search Report corresponding to counterpart Int'l Appln No. EP 14 17 4814.5 dated Jun. 9, 2015.
Australian Examination Report No. 1 corresponding to counterpart Int'l Appln No. AU 2014200584 dated Jun. 15, 2015.
European Office Action corresponding to counterpart Int'l Appln No. EP 13 180 881.8 dated Jun. 19, 2015.
European Office Action corresponding to counterpart Int'l Appln No. EP 14 157 195.0 dated Jul. 2, 2015.
Extended European Search Report corresponding to counterpart Int'l Appln No. EP 12 19 6902.6 dated Aug. 6, 2015.
Extended European Search Report corresponding to counterpart Int'l Appln No. EP 14 15 2060.1 dated Aug. 14, 2015.
Chinese Office Action corresponding to counterpart Int'l Appln No. CN 201210129787.2 dated Aug. 24, 2015.

\* cited by examiner

SURGICAL APPARATUS INCLUDING SURGICAL BUTTRESS

BACKGROUND

1. Technical Field

This application relates to a surgical apparatus, and more particularly, to a surgical buttress for use with a surgical stapling apparatus during operation of the stapling apparatus to apply a plurality of surgical staples to body tissue.

2. Background of Related Art

As medical and hospital costs continue to increase, surgeons are constantly striving to develop advanced surgical techniques. Advances in the surgical field are often related to the development of operative techniques which involve less invasive surgical procedures and reduce overall patient trauma. In this manner, the length of hospital stays can be significantly reduced, and, therefore, the hospital and medical costs can be reduced as well.

Although the present disclosure includes, but is not limited to use with endoscopic surgery, endoscopic surgery is one of the truly great advances in recent years to reduce the invasiveness of surgical procedures. Generally, endoscopic surgery involves incising through body walls for example, viewing and/or operating on the ovaries, uterus, gall bladder, bowels, kidneys, appendix, etc. There are many common endoscopic surgical procedures, including arthroscopy, laparoscopy (pelviscopy), gastroentroscopy and laryngobronchoscopy, just to name a few. Typically, trocars are utilized for creating the incisions through which the endoscopic surgery is performed. Trocar tubes or cannula devices are extended into and left in place in the abdominal wall to provide access for endoscopic surgical tools. A camera or endoscope is inserted through a relatively large diameter trocar tube which is generally located at the naval incision, and permits the visual inspection and magnification of the body cavity. The surgeon can then perform diagnostic and therapeutic procedures at the surgical site with the aid of specialized instrumentation, such as, forceps, cutters, applicators, and the like which are designed to fit through additional cannulas. Thus, instead of a large incision (typically 12 inches or larger) that cuts through major muscles, patients undergoing endoscopic surgery receive more cosmetically appealing incisions, between 5 and 10 millimeters in size. Recovery is, therefore, much quicker and patients require less anesthesia than traditional surgery. In addition, because the surgical field is greatly magnified, surgeons are better able to dissect blood vessels and control blood loss. Heat and water loss are greatly reduced as a result of the smaller incisions. In order to address the specific needs of endoscopic and/or laparoscopic surgical procedures, endoscopic surgical stapling devices have been developed and are disclosed in, for example, U.S. Pat. No. 5,040,715 (Green, et al.); U.S. Pat. No. 5,307,976 (Olson, et al.); U.S. Pat. No. 5,312,023 (Green, et al.); U.S. Pat. No. 5,318,221 (Green, et al.); U.S. Pat. No. 5,326,013 (Green, et al.); and U.S. Pat. No. 5,332,142 (Robinson, et al.).

In many surgical procedures, including those involved in open and endoscopic surgery, it is often necessary to staple tissue. It is especially challenging during endoscopic surgery because of the small openings through which the stapling of tissues must be accomplished. Instruments for this purpose can include two elongated members which are respectively used to capture or clamp tissue. Surgical devices wherein tissue is first grasped or clamped between opposing jaw member structures and then joined by surgical fasteners are well known in the art. Typically, one of the members carries a fastener cartridge which houses a plurality of staples arranged in at least two lateral rows while the other member has an anvil that defines a surface for forming the staple legs as the staples are driven from the staple cartridge. The fasteners are typically in the form of surgical staples but two part polymeric fasteners can also be utilized. Generally, the stapling operation is effected by cam bars or wedges that travel longitudinally through the staple cartridge, with the cam bars acting upon staple pushers to sequentially eject the staples from the staple cartridge. A knife can travel between the staple rows to longitudinally cut and/or open the stapled tissue between the rows of staples. Such instruments are disclosed, for example, in U.S. Pat. No. 3,079,606 and U.S. Pat. No. 3,490,675.

A later stapling apparatus disclosed in U.S. Pat. No. 3,499,591 applies a double row of staples on each side of the incision. This is accomplished by providing a disposable loading unit in which a cam member moves through an elongate guide path between two sets of staggered staple carrying grooves. Staple drive members are located within the grooves and are positioned in such a manner so as to be contacted by the longitudinally moving cam member to effect ejection of the staples from the staple cartridge of the disposable loading unit. U.S. Surgical, the assignee of the present application, has manufactured and marketed endoscopic stapling instruments for several years. Examples of such instruments include the Multifire ENDO GIA™ 30 and Multifire ENDO GIA™ 60 instruments. Other examples of such stapling apparatuses are disclosed in U.S. Pat. Nos. 4,429,695 and 5,065,929.

In stapling apparatuses of the general type described above, surgical buttress material may be used in combination with these instruments as reinforcement to staple lines. These instruments have provided significant clinical benefits. Nonetheless, improvements are possible, for example, by reducing the complexity of manufacture and/or application.

SUMMARY

According to one aspect, the present disclosure relates to a surgical stapling apparatus including a housing, an end effector, a plurality of fasteners, and one or more surgical buttresses. The housing supports a knife assembly including a knife. The end effector is secured to the housing and has first and second jaw member assemblies. The first jaw member assembly defines a plurality of fastener retaining slots. The second jaw member assembly defines a plurality of fastener forming pockets. The plurality of fasteners is disposed in the fastener retaining slots of the first jaw member assembly and configured and dimensioned to be formed by the fastener forming pockets of the second jaw member assembly. The one or more surgical buttresses have a body configured and dimensioned to substantially overlie one or both of at least some of the fastener retaining slots of the first jaw member assembly and at least some of the fastener forming pockets of the second jaw member assembly. The one or more surgical buttresses may be non-woven. The one or more surgical buttresses may be made from a material selected from the group comprising polyglytone 6211, glycolide, caprolactone, trimethylene carbonate, lactide and combinations thereof.

One or both of the first and second jaw member assemblies define a knife channel for the passage of the knife therethrough. The knife channel includes a plurality of lateral recesses extending therefrom. Portions of the body of the one or more surgical buttresses are disposed within the plurality of lateral recesses of the knife channel to secure the one or more surgical buttresses to one or both of the first jaw member assembly and the second jaw member assembly. Each lateral recess of the knife channel is defined by a plurality of walls.

Two or more of the plurality of walls of one or more of the lateral recesses taper in opposing directions relative to one another from a buttress receiving end of the respective lateral recess to form a flared configuration that increases a retention of a flared plug of the body of the one or more surgical buttresses within the respective lateral recess.

A second plurality of lateral recesses may extend from one or both of the fastener retaining slots of the first jaw member assembly and the fastener forming pockets of the second jaw member assembly. Portions of the body of the one or more surgical buttresses are disposed within the second plurality of lateral recesses to secure the one or more surgical buttresses to one or both of the first jaw member assembly and the second jaw member assembly.

Each lateral recess may extend substantially orthogonally to a longitudinal axis defined through the end effector. Portions of the body of the one or more surgical buttresses may be heat pressed into the lateral recesses.

According to another aspect, an end effector for a surgical stapling apparatus includes a first jaw member assembly, a second jaw member assembly, fasteners, one or more lateral recesses, and one or more surgical buttresses.

The first jaw member assembly defines fastener retaining slots and the second jaw member assembly defines fastener forming pockets. The fasteners are disposed in the fastener retaining slots of the first jaw member assembly and are configured and dimensioned to be formed by the fastener forming pockets of the second jaw member assembly.

The one or more lateral recesses extend from one or both of: the fastener retaining slots of the first jaw member assembly and the fastener forming pockets of the second jaw member assembly.

The one or more surgical buttresses have a body configured and dimensioned to substantially overlie one or both of: the fastener retaining slots of the first jaw member assembly and the fastener forming pockets of the second jaw member assembly. A portion of the body of the one or more surgical buttresses are disposed within the one or more lateral recesses to secure the one or more surgical buttresses to one or more of the first jaw member assembly and the second jaw member assembly. The one or more surgical buttresses may be non-woven. Portions of the body of the one or more surgical buttresses are heat pressed into the one or more lateral recesses. The one or more surgical buttresses may be made from a material selected from the group comprising polyglytone 6211, glycolide, caprolactone, trimethylene carbonate, lactide and combinations thereof.

One or both of the first and second jaw member assemblies may define a knife channel therethrough. The knife channel includes one or more lateral recesses extending therefrom for the reception of a portion of the one or more surgical buttresses.

Each lateral recess may be defined by a plurality of walls. Two or more of the plurality of walls of one or more of the lateral recesses taper in opposing directions relative to one another from a buttress receiving end of the respective lateral recess to form a flared configuration that increases a retention of a flared plug of the body of the one or more surgical buttresses within the respective lateral recess. The one or more lateral recesses may extend substantially orthogonally to a longitudinal axis defined through the end effector.

According to yet another aspect, a surgical stapling apparatus includes a housing, an end effector, a plurality of fasteners, and one or more surgical buttresses. The housing supports a knife assembly including a knife.

The end effector is secured to the housing and has first and second jaw member assemblies. One or both of the first and second jaw member assemblies defines a knife channel for the passage of the knife therethrough. The knife channel includes a first plurality of lateral recesses extending therefrom. The first jaw member assembly defines a plurality of fastener retaining slots and second jaw member assembly defines a plurality of fastener forming pockets. The plurality of fasteners is disposed in the fastener retaining slots of the first jaw member assembly and configured and dimensioned to be formed by the fastener forming pockets of the second jaw member assembly.

One or both of the first and second jaw member assemblies may include a second plurality of lateral recesses. The second plurality of lateral recesses extends from one or both of: the plurality of fastener retaining slots of the first jaw member assembly and the plurality of fastener forming pockets of the second jaw member assembly. As can be appreciated, the second plurality of lateral recesses may extend from the plurality of fasteners retaining slots of the first jaw member assembly and a third plurality of lateral recesses may extend from the plurality of fastener forming pockets of the second jaw member assembly. Each lateral recess is defined by a plurality of walls. Two or more of the plurality of walls of one or both of the lateral recesses taper in opposing directions relative to one another from a buttress receiving end of the respective lateral recess to form a flared configuration that increases a retention of a flared plug of the body of the one or more surgical buttresses within the respective lateral recess. Each lateral recess may extend substantially orthogonally to a longitudinal axis defined through the end effector.

The one or more surgical buttresses have a body configured and dimensioned to substantially overlie one or both of: at least some of the fastener retaining slots of the first jaw member assembly and at least some of the fastener forming pockets of the second jaw member assembly. The body of the one or more surgical buttresses is partially disposed within one or both of the first and second pluralities of lateral recesses to secure the one or more surgical buttresses to one or more of the first jaw member assembly and the second jaw member assembly. The one or more surgical buttresses may be non-woven and made from a material selected from the group comprising polyglytone 6211, glycolide, caprolactone, trimethylene carbonate, lactide and combinations thereof. Portions of the body of the one or more surgical buttresses may be heat pressed into the plurality of lateral recesses.

In another aspect of the present disclosure, a method of attaching a surgical buttress to the anvil assembly or the cartridge assembly of a surgical stapler comprises depositing an interlocking material onto a buttress body at one or more predetermined locations. Heat is applied to the buttress body to generate melt flow conditions of the interlocking material. A portion of the interlocking material at each of the predetermined locations is allowed to pass into at least one lateral recess defined in the cartridge assembly or anvil assembly. The interlocking material is solidified so that the interlocking material mechanically interlocks within the at least one lateral recess.

The interlocking material can be overmolded onto the buttress body. The interlocking material may be a degradable polymer. The buttress body can be porous. The method may further comprise allowing the interlocking material to solidify within pores of the buttress body.

In certain embodiments, pressure is applied to the interlocking material, the buttress body, or both. A portion of the degradable polymer may be passed into pores defined in the buttress body as the interlocking material is passed into the at least one lateral recess. The method can further comprise applying heat to solidify the interlocking material. The interlocking material may have a melting temperature below that of buttress body. The interlocking material can be a degradable polymer including one or more of the following: glycolide, glycolic acid, lactic acid, caprolactone, trimethylene carbonate, and lactide.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION OF EMBODIMENTS

As used herein, the term "clinician" refers to a doctor, a nurse, or any other care provider and may include support personnel. Particular embodiments of the present disclosure will be described herein with reference to the accompanying drawings. As shown in the drawings and as described throughout the following description, and as is traditional when referring to relative positioning on an object, the term "proximal" refers to the end of the apparatus that is closer to the clinician and the term "distal" refers to the end of the apparatus that is farther from the clinician. In the following description, well-known functions or constructions are not described in detail to avoid obscuring the present disclosure in unnecessary detail.

In general, linear stapling apparatuses, including open and endoscopic devices, can have two elongated members which are respectively used to capture or clamp tissue. Typically, one of the members carries a staple cartridge which houses a plurality of staples arranged in at least two lateral rows while the other member has an anvil that defines a surface for forming the staple legs as the staples are driven from the staple cartridge. Generally, the stapling operation is effected by cam bars that travel longitudinally through the staple cartridge, with the cam bars acting upon staple pushers to sequentially eject the staples from the staple cartridge. A knife can travel between the staple rows to longitudinally cut and/or open the stapled tissue between the rows of staples. Such an instrument is disclosed, for example, in U.S. Pat. No. 6,202,914, the entire content of which is incorporated herein by reference.

Some stapling apparatuses apply a double row of staples on each side of the incision. This is accomplished by providing a disposable loading unit in which a cam member moves through an elongate guide path between two sets of staggered staple carrying grooves. Staple drive members are located within the grooves and are positioned in such a manner so as to be contacted by the longitudinally moving cam member to effect ejection of the staples from the staple cartridge of the disposable loading unit. An example of such a stapling apparatus is disclosed in U.S. Pat. No. 5,065,929, the entire content of which is incorporated herein by reference.

Some of the instruments described above were designed for use in conventional surgical procedures wherein surgeons have direct manual access to the operative site. However, in endoscopic or laparoscopic procedures, surgery is performed through a small incision or through a narrow cannula inserted through small entrance wounds in the skin. In order to address the specific needs of endoscopic and/or laparoscopic surgical procedures, endoscopic surgical stapling devices have been developed and are disclosed in, for example, U.S. Pat. No. 5,865,361, the entire content of which is incorporated herein by reference.

Figure 1:
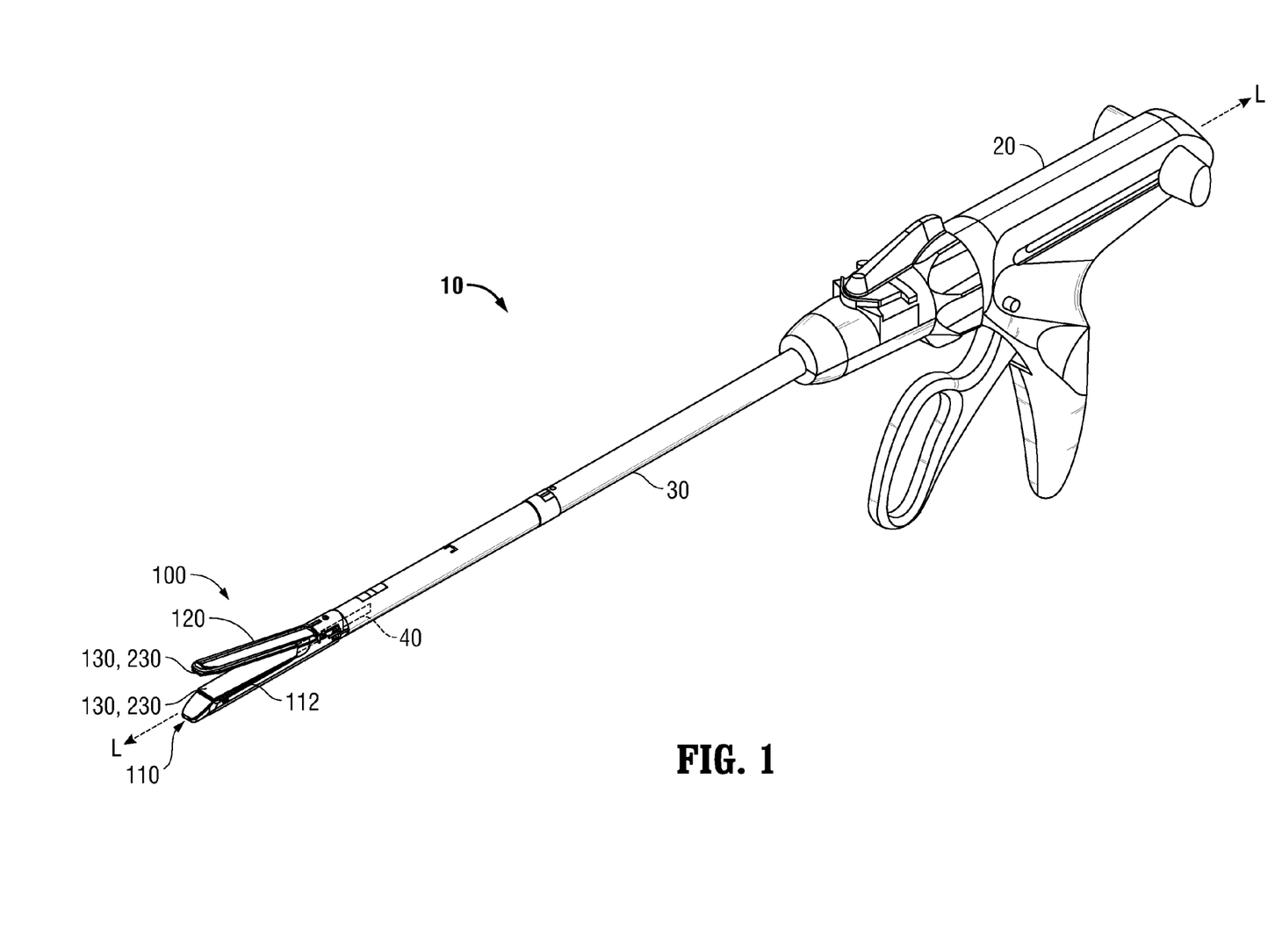
FIG. 1 is a perspective view of an endoscopic surgical stapling apparatus with surgical buttresses supported thereon according to the present disclosure.

Referring now to the drawings, in which like reference numerals identify identical or substantially similar parts throughout the several views, FIG. 1 illustrates a surgical stapling apparatus 10 in accordance with the present disclosure that may be arranged for use with minimally invasive or open stapling procedures. The surgical stapling apparatus 10 includes a housing 20 and an elongate member 30 that extends distally from the housing 20. A distal end of the elongate member 30 supports a proximal end of an end effector 100. The end effector 100 defines a longitudinal axis "L" between the proximal and distal ends of the end effector 100 and includes a first jaw member and/or cartridge assembly 110 that is configured to selectively receive a staple cartridge 112 and a second jaw member and/or anvil assembly 120. The cartridge assembly 110 and the anvil assembly 120 are pivotably coupled at proximal ends thereof and may each support a surgical buttress 130, 230 (as used herein, "surgical buttress" includes a pledget, gasket, buttress, or staple line reinforcement structure). The staple cartridge 112 houses staples and/or other surgical fasteners other than staples. The end effector can be part of a removable and replaceable loading unit, so that a new cartridge, anvil and staple applying assembly are supplied with each firing. The cartridge assembly 110 and the staple cartridge 112 may be selectively replaceable, as part of a replaceable loading unit, or otherwise.

Figure 2:
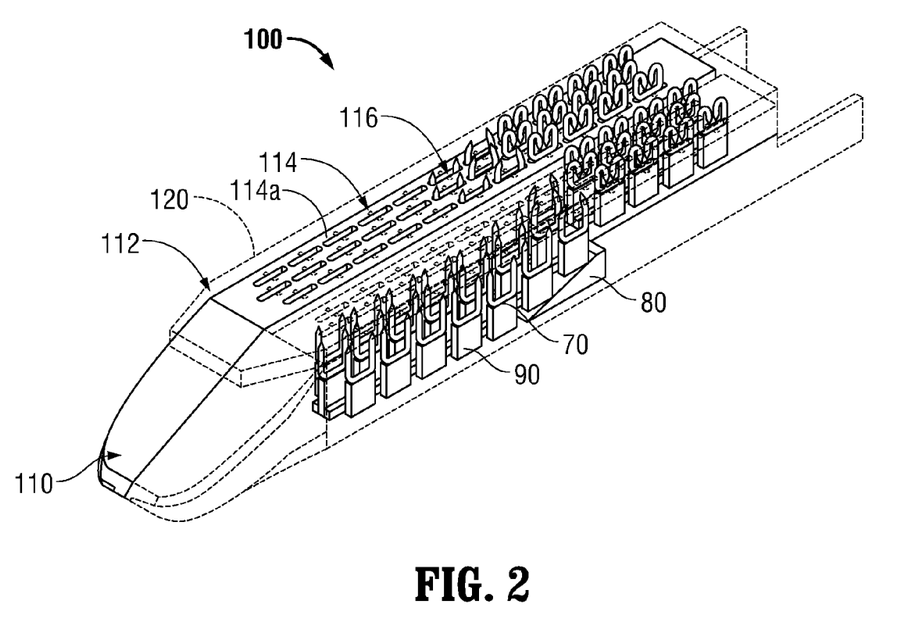
FIG. 2 is an enlarged perspective view illustrating an end effector of the presently disclosed surgical stapling apparatus during a fastener applying operation as fasteners are being sequentially fired.
Figure 3:
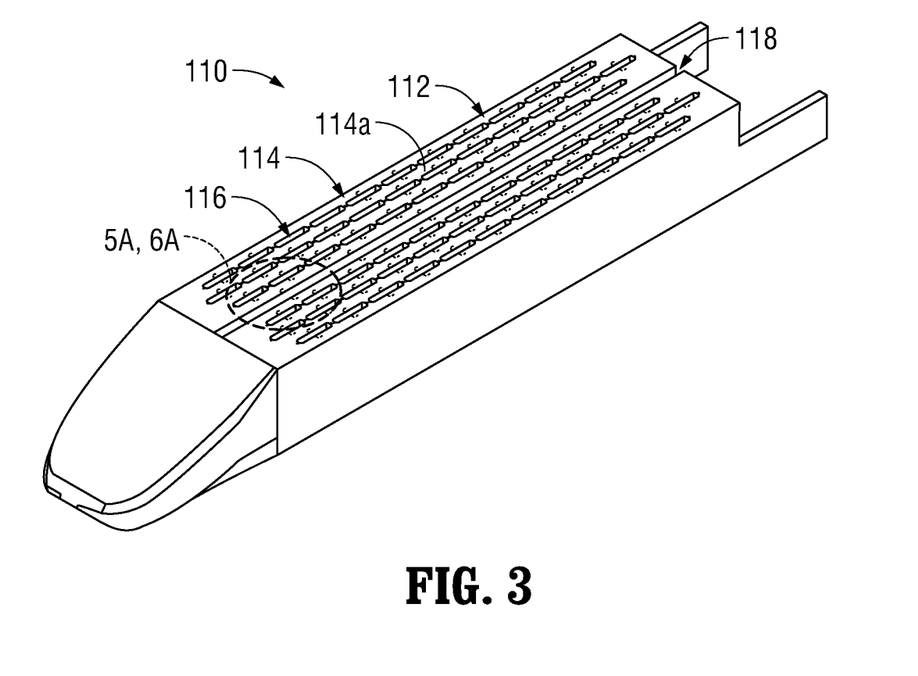
FIG. 3 is a top perspective view of one embodiment of a cartridge assembly of the end effector illustrated in FIG. 2.
Figure 4:
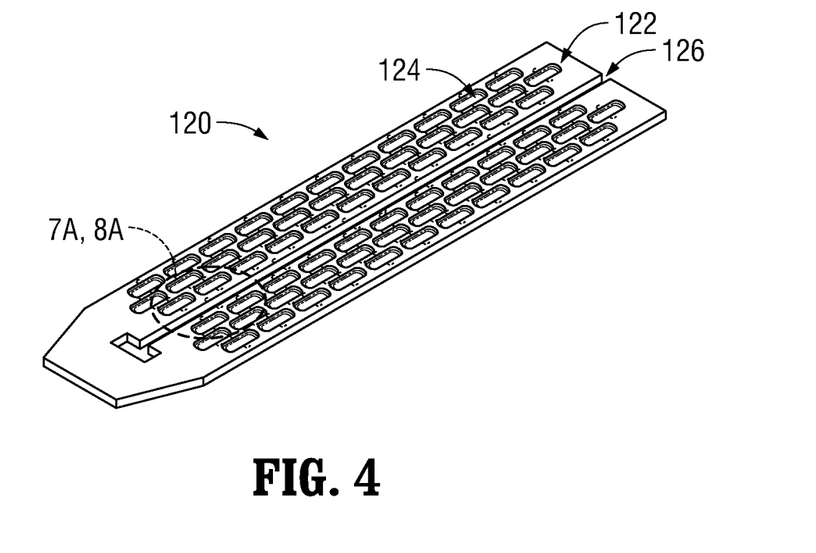
FIG. 4 is a bottom perspective view of one embodiment of an anvil assembly of the end effector illustrated in FIG. 2.

With reference to FIGS. 2-3, the staple cartridge 112 includes a cartridge housing 114 including a tissue contacting surface 114a having a plurality of rows of fastener retaining slots (also referred to herein as stapling apparatus slots and fastener slots) 116 formed therein that house a plurality of fasteners or staples 70. The staple cartridge 112 defines a cartridge knife channel 118 between proximal and distal ends of the staple cartridge 112 that is configured to receive a knife 40 (FIG. 1) that translates distally through the cartridge knife channel 118 to cut tissue clamped between the cartridge assembly 110 and the anvil assembly 120. Also referring to FIG. 4, the plurality of staples 70 may be sequentially formed in fastener forming pockets 124 defined in a tissue contacting surface 122 of the anvil assembly 120 upon a distal advancement of a cam bar and/or a sled 80 supported in the cartridge housing 114 into a plurality of staple pusher members 90 supported in the cartridge housing 114. The anvil assembly 120 defines an anvil knife channel 126 between proximal and distal ends of the anvil assembly 120 that receives the knife 40 as the knife 40 translates distally through the cartridge knife slot 118.

Figure 5A:
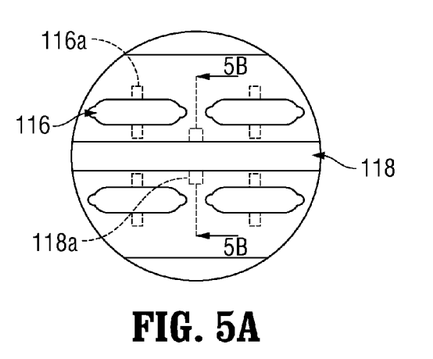
FIG. 5A is an enlarged top view of the indicated area of detail of the cartridge assembly shown in FIG. 3.
Figure 5B:
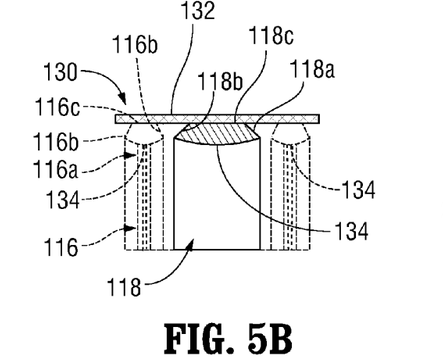
FIG. 5B is a cross-sectional view, as taken through 5B-5B of FIG. 5A, of the indicated area of detail of the cartridge assembly shown in FIG. 5A with a surgical buttress shown secured to the cartridge assembly.

As depicted in FIGS. 5A-5B, one or more of the fastener slots 116 of the cartridge assembly 110 may include one or more lateral recesses or cut-outs 116a that extend transversely (relative to the longitudinal axis "L" extending through the end effector 100) or substantially transversely (i.e., non-orthogonally) therefrom that are defined within the staple cartridge 112 and are configured to receive a portion of the surgical buttress 130 therein to secure the surgical buttress 130 to the cartridge assembly 110. As shown in FIG. 5B, each lateral recess 116a of the fastener slot 116 is defined by a plurality of walls 116b. The plurality of walls 116b may be tapered at any suitable angle. Two or more of the walls 116b may be tapered in opposing directions relative to one another from a buttress receiving end 116c of the fastener slot 116 to form a flared configuration.

Similarly, the knife channel 118 of the cartridge assembly 110 may include one or more lateral recesses or cut-outs 118a that extend transversely or substantially transversely therefrom and are defined within the staple cartridge 112. The lateral recess 118a is configured to receive a portion of a surgical buttress 130 therein to secure the surgical buttress 130 to the cartridge assembly 110. As shown in FIG. 5B, each lateral recess 118a of the knife channel 118 is defined by a plurality of walls 118b. The plurality of walls 118b may be tapered at any suitable angle. Two or more of the plurality of walls 118b may be tapered in opposing directions relative to one another from a buttress receiving end 118c of the knife channel 118 to form a flared configuration.

Figure 7A:
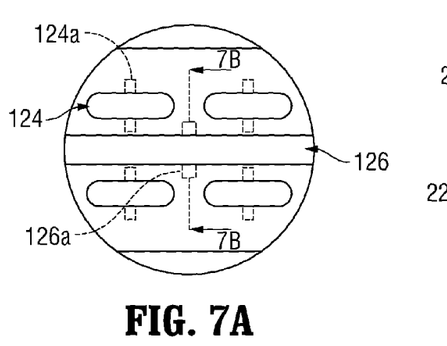
FIG. 7A is an enlarged bottom view of the indicated area of detail of the anvil assembly shown in FIG. 4.
Figure 7B:
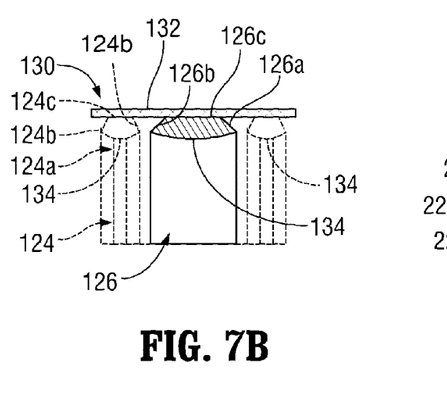
FIG. 7B is a cross-sectional view, as taken through 7B-7B of FIG. 7A, of the indicated area of detail of the anvil shown in FIG. 7A with a surgical buttress shown secured to the anvil assembly.

Turning now to FIGS. 7A-7B, one or more of the fastener forming pockets 124 of the anvil plate of the anvil assembly 120 may include one or more lateral recesses or cut-outs 124a extending transversely or substantially transversely therefrom that are defined within the anvil plate of the anvil assembly 120 and are configured to receive a portion of the surgical buttress 130 therein to secure the surgical buttress 130 to the anvil assembly 120. As shown in FIG. 7B, each lateral recess 124a of the fastener forming pockets 124 is defined by a plurality of walls 124b. The plurality of walls 124b may be tapered at any suitable angle. Two or more of the walls 124b may be tapered in opposing directions relative to one another from a buttress receiving end 124c of the fastener forming pocket 124 to form a flared configuration.

Similarly, the knife channel 126 of anvil assembly 120 may include one or more lateral recesses 126a that extend transversely or substantially transversely therefrom and are defined within the anvil assembly 120. The lateral recess 126a (see FIG. 7A) is configured to receive a portion of the surgical buttress 130 therein to secure the surgical buttress 130 to the anvil assembly 120. As shown in FIG. 7B, each lateral recess 126a of knife channel 126 is defined by a plurality of walls 126b. The plurality of walls 126b may be tapered at any suitable angle. Two or more of the walls 126b may be tapered in opposing directions relative to one another from a buttress receiving end 126c of the knife channel 126 to form a flared configuration.

Notably, the flared configurations of the lateral recesses 116a, 118a of the cartridge assembly 110 facilitate the securement of the surgical buttress 130 adjacent to/against the tissue contacting surface 114a of the staple cartridge 112 of the cartridge assembly 110. Similarly, the flared configurations of the lateral recess 124a, 126a of the anvil assembly 120 facilitate the securement of the surgical buttress 130 adjacent to/against the tissue contacting surface 122 of an anvil plate of the anvil assembly 120, as will be described in greater detail below.

Referring again to FIGS. 5B and 7B, the surgical buttress 130, which may be porous, non-porous, a mesh or knit, woven, and/or non-woven material, includes a buttress body 132 and one or more flared plugs 134 (FIG. 5B) that extend from the buttress body 132 opposite a tissue contacting surface of the buttress body 132. The buttress body 132, which has a substantially rectangular shape, is configured to be secured to one or both of the cartridge assembly 110 and the anvil assembly 120 to provide fastener-line reinforcement for the plurality of staples 70 following the firing of the surgical stapling apparatus. In any of the embodiments disclosed herein, the buttress body 132 can be shaped as described in U.S. application Ser. No. 13/419,565, filed Mar. 14, 2012, the entire disclosure of which is hereby incorporated by reference herein, and U.S. Pat. No. 8,011,555, the entire disclosure of which is hereby incorporated by reference herein.

When secured to the cartridge assembly 110, the buttress body 132 overlies one or more of the fastener slots 116 of the tissue contacting surface 114a of the staple cartridge 112 such that a flared plug 134 is supported within a lateral recess 116a, 118a of the staple cartridge 112 by virtue of the flared configuration of the respective lateral recess 116a, 118a to maintain the buttress body 132 supported adjacent to/against the tissue contacting surface 114a of the staple cartridge 112. In this regard, the flared configuration of the respective lateral recess 116a, 118a increases a retention of the flared plug 134 within the respective lateral recess 116a, 118a to secure the surgical buttress 130 to the staple cartridge 112 of the cartridge assembly 110.

In any of the embodiments disclosed herein, adhesive, a piece of suture, strap, cable, thread, etc., and/or other material can additionally be used to retain the buttress. Furthermore, it is contemplated that the buttress is retained at least in part by mechanical interlocking, friction, etc.

When secured to the anvil assembly 120, the buttress body 132 overlies one or more of the fastener forming pockets 124 of the tissue contacting surface 122 of the anvil assembly 120 such that a flared plug 134 is supported within a lateral recess 124a, 126a of the anvil assembly 120 by virtue of the flared configuration of the respective lateral recess 124a, 126a to maintain the buttress body 132 supported adjacent to/against the tissue contacting surface 122 of the anvil plate of the anvil assembly 120. In this regard, the flared configuration of the respective lateral recess 124a, 126a increases retention of the flared plug 134 within the respective lateral recess 124a, 126a to secure the surgical buttress 130 to the anvil assembly 120.

Figure 6A:
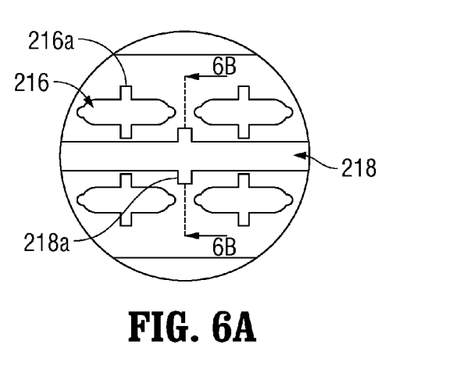
FIG. 6A is an enlarged top view of the indicated area of detail of another embodiment of the cartridge assembly shown in FIG. 3.
Figure 6B:
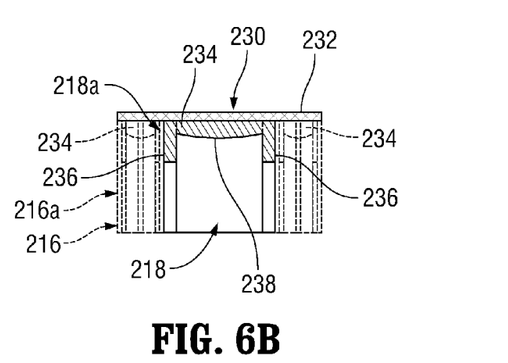
FIG. 6B is a cross-sectional view, as taken through 6B-6B of FIG. 6A, of the indicated area of detail of the cartridge assembly shown in FIG. 6A with a surgical buttress shown secured to the cartridge assembly.

As depicted in FIGS. 6A-6B, one embodiment of a cartridge assembly includes a stapling apparatus cartridge defining a plurality of fastener slots 216 and a knife channel 218. One or more of the fastener slots 216 include one or more lateral recesses or cut-outs 216a. The lateral recess 216a extends transversely or substantially transversely from the fastener slot 216. The knife channel 218 includes one or more lateral recesses or cut-outs 218a which extend transversely or substantially transversely from the knife channel 218. The lateral recesses 216a, 218a are defined through the tissue contacting surface 114a of the staple cartridge 114 and are configured to receive a portion of a surgical buttress 230 therein to secure the surgical buttress 230 to the cartridge assembly, which will be described in greater detail below.

Figure 8A:
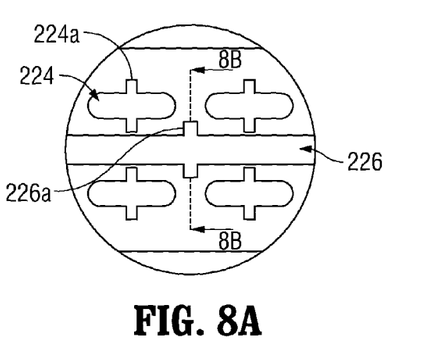
FIG. 8A is an enlarged bottom view of the indicated area of detail of another embodiment of the anvil assembly shown in FIG. 4.
Figure 8B:
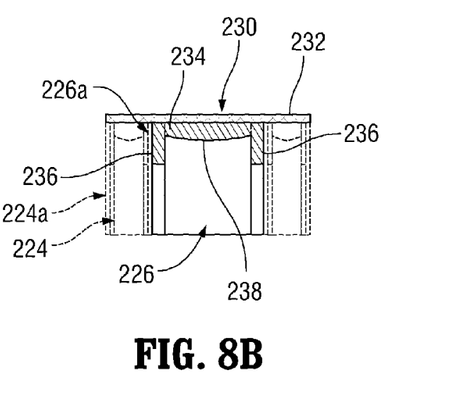
FIG. 8B is a cross-sectional view, as taken through 8B-8B of FIG. 8A, of the indicated area of detail of the anvil shown in FIG. 8A with a surgical buttress shown secured to the anvil assembly.

As depicted in FIGS. 8A-8B, one embodiment of an anvil assembly defines a plurality of fastener forming pockets 224 and a knife channel 226 in an anvil plate thereof. One or more of the fastener forming pockets 224 include one or more lateral recesses or cut-outs 224a that extend transversely or substantially transversely from the fastener forming pockets 224 and the knife channel 226 includes one or more lateral recesses or cut-outs 226a that extend transversely or substantially transversely from the knife channel 226. The lateral recesses 224a, 226a are defined through the tissue contacting surface 122 of the anvil plate of the anvil assembly and are configured to receive a portion of the surgical buttress 230 therein to secure the surgical buttress 230 to the anvil, which will be described in greater detail below.

Referring again to FIGS. 6B and 8B, the surgical buttress 230, which may be porous, non-porous, woven, mesh or knit, and/or non-woven material, includes a buttress body 232 and one or more plugs 234 that extend from the buttress body 232 opposite a tissue contacting surface of the buttress body 232. The buttress body 132, which has a substantially rectangular shape, is configured to be secured to one or both of the cartridge assembly 110 and the anvil assembly 120 to provide fastener-line reinforcement for the plurality of staples 70 following the firing of the surgical stapling apparatus. The plug 234 includes a pair of side segments 236 extending from opposed sides of a body segment 238 that secure within lateral recesses 216a, 218a, 224a, 226a of anvil and cartridge assembly to support the buttress body 232 on one or both of the anvil assembly and cartridge assembly.

More particularly, when secured to the cartridge assembly, the buttress body 232 overlies one or more of the fastener slots 216 of the tissue contacting surface of the staple cartridge such that the plug 234 of the surgical buttress 230 is supported within a lateral recess 216a, 218a of the staple cartridge to maintain the buttress body 232 supported adjacent to/against the tissue contacting surface of the staple cartridge. Similarly, when secured to the anvil assembly, the buttress body 232 overlies one or more of the fastener forming pockets 224 of the anvil assembly 120 such that each plug 234 is supported within a lateral recess 224a, 226a defined in the anvil plate of the anvil assembly to maintain the buttress body 232 supported adjacent to/against the tissue contacting surface of the anvil plate of the anvil assembly.

Additionally or alternatively, the surgical buttresses 130, 230 may be secured to the cartridge assembly and the anvil by any suitable or mechanical connection (e.g., snap-fit, hook and loop type (Velcro®, Velcro Industries B.V. LTD LIAB CO NETHERLANDS) fasteners, straps, threads, etc.).

In embodiments, at least a portion of the surgical buttress 130, 230 may be made from biodegradable materials selected from the following group: natural collagenous materials, cat gut, and synthetic resins including those derived from alkylene carbonates, trimethylene carbonate, tetramethylene carbonate, caprolactone, valerolactone, dioxanone, polyanhydrides, polyesters, polyacrylates, polymethylmethacrylates, polyurethanes, glycolic acid, lactic acid, glycolide, lactide, polyhydroxy butyrates, polyorthoester, polyhydroxy alkanoates, homopolymers thereof, and copolymers thereof. In embodiments, at least a portion of the surgical buttress 130, 230 may be made from non-biodegradable materials selected from the following group: polyolefins, polyethylene, polydimethylsiloxane, polypropylene, copolymers of polyethylene and polypropylene, blends of polyethylene and polypropylene, ultra high molecular weight polyethylene, polyamides, polyesters, polyethylene terephthalate, polytetrafluoroethylene, polyether-esters, polybutester, polytetramethylene ether glycol, 1,4-butanediol, and polyurethanes. In embodiments, the surgical buttresses 130, 230 or portions thereof, may be a non-woven material selected from the group including polyglytone 6211, glycolide, caprolactone, trimethylene carbonate, lactide and combinations thereof.

For example, to attach one of the surgical buttresses 130, 230 to any of the embodiments of the anvil or the cartridge assembly, a degradable polymer may be overmolded or deposited onto the buttress body 132, 232, which is porous, at one or more predetermined locations. Next, heat and pressure are applied to the buttress 130, 230 to generate melt flow conditions. Then, under the melt flow conditions, a portion of the degradable polymer at each predetermined location is passed into a lateral recess 116a, 118a, 224a, 226a while a portion of the degradable polymer is simultaneously passed into the pores defined in the buttress body 132, 232. The degradable polymer is then solidified to mechanically interlock within the respective lateral recess 116a, 118a, 224a, 226a and within the pores of the buttress body 132, 232. In particular, the degradable polymer solidifies into the flared plug 134 or plug 234 to secure to the buttress body 132, 232 to one or both of the anvil and cartridge assembly adjacent to/against the tissue contacting surfaces of the respective anvil and cartridge assembly.

The degradable polymer may have a melting temperature below that of buttress body 132, 232 so that the degradable polymer can be melted without disrupting the physical properties of the buttress body 132, 232. In embodiments, the degradable polymer may include Caprosyn material which is an absorbable synthetic material prepared from POLYGLYTONE 6211, which includes glycolide, caprolactone, trimethylene carbonate, and Lactide. Caprosyn material has a melt temperature range of 125-145 degrees Celsius. The buttress body 132, 232 may include a synthetic material prepared from gylcolide (65 percent) and trimethylne carbonate (35 percent) in a 10 gallon Helcone reactor. In embodiments, the buttress body 132, 232 may include Maxon material which is a synthetic material prepared from polyglyconate, a copolymer of glycolic acid and trimethylene carbonate. The material of the buttress body 132, 232 may have a melting temperature between 185 degrees Celsius and 220 degrees Celsius. In embodiments, the buttress body 132, 232 may have a melting temperature between 210 degrees Celsius and 220 degrees Celsius and/or between 185 degrees Celsius and 200 degrees Celsius.

During operation of the surgical stapling apparatus 10, the cartridge assembly 110 and the anvil assembly 120 are clamped against tissue of a patient. As illustrated in FIG. 2, the surgical stapling apparatus 10 is fired to deploy the fasteners 70 through the fastener slots 116, 216. Upon firing, the fasteners 70 pass through the fastener slots 116, 216 driving any plugs 134, 234 positioned in the lateral recesses 116a, 216a of the staple cartridge 112 out of the respective lateral recesses 116a, 216a. Meanwhile, legs of the fasteners 70 penetrate through the tissue and the buttress body 132, 232. The fasteners 70 are then formed against the fastener forming pockets 124, 224 of the anvil assembly 120 thereby affixing the buttress body 132, 232 to the tissue and pulling any plugs 134, 234 positioned in lateral recesses 124a, 224a out of the respective lateral recesses 124a, 224a of the anvil plate of the anvil assembly 120.

Concomitantly therewith, the knife 40 translatably disposed within the end effector 100, cuts through the tissue clamped between the cartridge assembly 110 and the anvil assembly 120 and through at least a portion of the buttress body 132, 232. As the knife 40 translates along the knife channel 118, 126, the knife 40 mechanically disrupts any plug 134, 234 positioned in the knife channel 118, 126. In particular, a leading edge of the knife 40 presses against and cuts any plug 134, 234 distally from a proximal end thereof and a knife bar positioned proximally of the leading edge of the knife 40 fills the width of the knife channel 118, 126 further pushing against any plug 134, 234 positioned in the knife channel 118, 126 and displaces or breaks the plug 134, 234 away from the respective lateral recess 118a, 126a of the knife channel 118, 126.

As can be appreciated, embodiments of the staple cartridges and the anvil assemblies of the presently disclosed surgical stapling apparatus may be configured to have any suitable arrangement of any of the embodiments of the lateral recesses to accommodate any of the embodiments of the plugs of any of the embodiments of the buttresses. Similarly, embodiments of the buttresses of the presently disclosed surgical stapling apparatus may be configured to have any suitable arrangement of any of the embodiments of the plugs to engage with any of the embodiments of the lateral recesses of the embodiments of the cartridge assembly or anvil. Indeed, any combination of any of the components of the presently disclosed surgical stapling apparatus is within the scope of the present disclosure.

In certain embodiments, the knife can be configured and arranged to cut through the surgical buttress 130, 230 prior to firing. Alternatively, the surgical buttress 130, 230 can be cut with shears, or can include perforations or frangible features.

While the cartridge assembly 110 may be a single use loading unit, the user may remove the single use loading unit, or portions thereof, from the surgical stapling apparatus 10 and subsequently dispose the single use loading unit in its entirety, or portions thereof. If further application is necessary, a user may replace the spent or fired single use loading unit by mounting a new single use loading unit, in the form of a new cartridge assembly and a new surgical buttress 130, 230, onto the surgical stapling apparatus 10. The user may then repeat a fastening process with the new single use loading unit.

It is further contemplated that, if desired, an end user may remove surgical buttress 130, 230 from cartridge assembly 110 or anvil assembly 120 prior to a use of surgical stapling apparatus 10.

In embodiments, the surgical buttress is configured for use with surgical fastening devices for simultaneously applying an array of surgical fasteners, e.g., staples or other types of fasteners that are known in the art. Such devices are used for joining body tissue such as, for example, intestinal and gastric walls with spaced parallel rows of longitudinally aligned fasteners. These surgical fastening devices reduce the time of wound closure in a surgical procedure.

Typically, these devices include a fastener holder disposed on one side of the tissue to be joined, and an anvil assembly parallel to the fastener holder on the other side of the tissue to be fastened. The fastener holder is moved linearly towards the anvil assembly so that the tissue is clamped between them. The fasteners are driven from the fastener holder so that the ends of the fasteners pass through the tissue and form finished fasteners as they make contact with the anvil assembly, thereby producing an array of finished fasteners in the tissue. The fasteners can be one or two piece and made of metal, non-absorbable polymers, or bioabsorbable polymers such as plyglycolide, polylactide, and copolymers thereof.

U.S. Pat. No. 5,137,198 to Nobis et al. ("Nobis") discloses a fastener applying device including a cartridge that is advanced towards an anvil assembly by an advancing mechanism. The advancing mechanism includes a first actuator member for advancing the cartridge towards the anvil assembly at an accelerated rate and a second actuator member spaced from the first actuator member for incrementally advancing the cartridge towards the anvil assembly.

Typically, these fastener applying devices include a pusher bar that is advanced over a predetermined stroke to interact with and eject the fasteners from the cartridge. At least one driver is positioned within the cartridge between the distal end of the pusher bar and the fasteners such that the pusher bar advances the drivers into engagement with the fasteners. The length of the drivers may be varied to facilitate ejection of different size fasteners from a fastener applying device having a fixed pusher bar stroke. Such instruments are disclosed, for example, in U.S. Pat. No. 5,964,394, the entire content of which is incorporated herein by reference.

Persons skilled in the art will understand that the structures and methods specifically described herein and illustrated in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the subject matter of the present disclosure is not to be limited by what has been particularly shown and described.

What is claimed is:

1. A surgical stapling apparatus, comprising:
an end effector having first and second jaw member assemblies, at least one of the first and second jaw member assemblies defining a knife channel for the passage of a knife therethrough, the knife channel including a plurality of lateral recesses extending therefrom, wherein the first jaw member assembly defines a plurality of fastener retaining slots, the second jaw member assembly defining a plurality of fastener forming pockets;
a plurality of fasteners disposed in the fastener retaining slots of the first jaw member assembly and being configured to be deformed by the fastener forming pockets of the second jaw member assembly; and
at least one surgical buttress having a body configured to substantially overlie at least one of the fastener retaining slots of the first jaw member assembly, at least some of the fastener forming pockets of the second jaw member assembly, or both;
wherein portions of the body of the at least one surgical buttress are disposed within the plurality of lateral recesses of the knife channel to secure the at least one surgical buttress to at least one of the first jaw member assembly and the second jaw member assembly, each lateral recess of the knife channel is defined by a plurality of walls, wherein at least two of the plurality of walls of at least one of the lateral recesses taper in opposing directions relative to one another from a buttress receiving end of the respective lateral recess to form a flared configuration, whereby the flared configuration increases retention of a flared plug of the body of the at least one surgical buttress within the respective lateral recess.

2. The surgical stapling apparatus of claim 1, wherein the at least one surgical buttress is a non-woven material.

3. The surgical stapling apparatus of claim 1, wherein a second plurality of lateral recesses extends from at least one of the fastener retaining slots of the first jaw member assembly, the fastener forming pockets of the second jaw member assembly, or both;
wherein portions of the body of the at least one surgical buttress are disposed within the second plurality of lateral recesses to secure the at least one surgical buttress to at least one of first jaw member assembly and the second jaw member assembly.

4. The surgical stapling apparatus of claim 1, wherein each lateral recess extends substantially orthogonally to a longitudinal axis defined through the end effector.

5. The surgical stapling apparatus of claim 1, wherein portions of the body of the at least one surgical buttress are heat pressed into the lateral recesses.

6. The surgical stapling apparatus of claim 1, wherein the at least one surgical buttress is made from a material selected from a group comprising glycolide, caprolactone, trimethylene carbonate, lactide and combinations thereof.

7. An end effector for a surgical stapling apparatus, comprising:
a first jaw member assembly defining fastener retaining slots;
a second jaw member assembly defining fastener forming pockets;
fasteners disposed in the fastener retaining slots of the first jaw member assembly and being configured to be formed by the fastener forming pockets of the second jaw member assembly;
at least one lateral recess extending from at least one of the fastener retaining slots of the first jaw member assembly, at least one of the fastener forming pockets of the second jaw member assembly, or both;
and
at least one surgical buttress having a body configured to substantially overlie at least one of the fastener retaining slots of the first jaw member assembly, at least one of the fastener forming pockets of the second jaw member assembly, or both;
a portion of the body of the at least one surgical buttress being disposed within the at least one lateral recess to secure the at least one surgical buttress to at least one of the first jaw member assembly and the second jaw member assembly;
wherein at least one of the first and second jaw member assemblies defines a knife channel therethrough, the knife channel including at least one lateral recess extending therefrom for the reception of a portion of the at least one surgical buttress, each lateral recess is defined by a plurality of walls, wherein at least two of the plurality of walls of at least one of the lateral recesses taper in opposing directions relative to one another from a buttress receiving end of the respective lateral recess to form a flared configuration, whereby the flared configuration increases retention of a flared plug of the body of the at least one surgical buttress within the respective lateral recess.

8. The end effector of claim 7, wherein the at least one surgical buttress is a non-woven material.

9. The end effector of claim 7, wherein at least one of the lateral recesses extends substantially orthogonally to a longitudinal axis defined through the end effector.

10. The end effector of claim 7, wherein portions of the body of the at least one surgical buttress are heat pressed into at least one of the lateral recesses.

11. The end effector of claim 7, wherein the at least one surgical buttress is made from a material selected from a group comprising glycolide, caprolactone, trimethylene carbonate, lactide and combinations thereof.

* * * * *